(12) United States Patent
Marion

(10) Patent No.: US 12,123,811 B2
(45) Date of Patent: Oct. 22, 2024

(54) ENVIRONMENTAL WATER SAMPLING DRONE ATTACHMENT DEVICE

(71) Applicant: Daniel Marion, Vero Beach, FL (US)

(72) Inventor: Daniel Marion, Vero Beach, FL (US)

( * ) Notice: Subject to any disclaimer, the term of this patent is extended or adjusted under 35 U.S.C. 154(b) by 326 days.

(21) Appl. No.: 17/589,371

(22) Filed: Jan. 31, 2022

(65) Prior Publication Data

US 2022/0244145 A1 Aug. 4, 2022

Related U.S. Application Data

(60) Provisional application No. 63/143,327, filed on Jan. 29, 2021.

(51) Int. Cl.
*G01N 1/12* (2006.01)
*B64D 47/00* (2006.01)
*G01N 33/18* (2006.01)

(52) U.S. Cl.
CPC ............... *G01N 1/12* (2013.01); *B64D 47/00* (2013.01); *G01N 33/18* (2013.01)

(58) Field of Classification Search
CPC . G01N 1/12; G01N 33/18; G01N 1/10; B64D 47/00; B64U 2101/60
USPC ...... 73/863, 863.31, 863.51–863.57, 864.31, 73/864.51, 864.63; 248/682, 689, 318, 248/323, 324, 327
See application file for complete search history.

(56) References Cited

U.S. PATENT DOCUMENTS

| | | | |
|---|---|---|---|
| 4,744,256 A | | 5/1988 | Niskin |
| 5,739,439 A | * | 4/1998 | Gruidel ............... G01N 1/26 73/863.31 |
| 9,606,028 B2 | | 3/2017 | Detweiller |
| 2017/0328814 A1 | | 11/2017 | Castendyk |

FOREIGN PATENT DOCUMENTS

| CN | 205879594 U | 1/2017 |
|---|---|---|
| CN | 106525493 A | 3/2017 |

* cited by examiner

*Primary Examiner* — Robert R Raevis

(57) ABSTRACT

An environmental water sampling drone attachment device has a mounting prong, a pivoting clamp, a pivot axle, at least one mounting harnesses, and at least one container The mounting prong is a shaft that attaches the present invention to an Unmanned Aerial Vehicle (UAV). The pivoting clamp is used to hold the pivot axle in place. The pivot axle can rotate within the pivoting clamp and is fixed to the mounting harness. The mounting harness holds and rotates the container. The container is a device that gathers water when placed into a body of water. Thus, the container is held by the mounting harness when gathering water samples until the container is removed by a user. As a result, this device is able to gather water samples and hold the water samples within the container until the water samples need to be removed by the user.

20 Claims, 7 Drawing Sheets

ENVIRONMENTAL WATER SAMPLING DRONE ATTACHMENT DEVICE

The current application claims a priority to the U.S. provisional patent application Ser. No. 63/143,327 filed on Jan. 29, 2021. The current application is filed on Jan. 31, 2022 while Jan. 29, 2022 was on a weekend.

FIELD OF THE INVENTION

The present invention relates generally to an environmental water sampling drone attachment device. More specifically, the present invention is a device that can attach to an Unmanned Air Vehicle to gather water samples from a body of water.

BACKGROUND OF THE INVENTION

Water sampling is a common practice in many industries for a variety of different purposes. Much of the water sampling methods are completed daily to fulfill regulatory requirements and to further run the water through tests to maintain safety. Water quality is usually sampled and analyzed within laboratories with the necessary equipment improving over time with technology advances. Techniques and technology used to gather the water samples however has not improved much over time with individuals opting to retrieve water samples from lakes and large bodies of water by foot or by boat. The present invention intends to gather water samples in areas that are not easily accessible by foot, such as lakes, ponds, rivers, seas, and oceans. An Unmanned Air Vehicle (UAV) that lands on water utilizes the present invention with at least one container that can rotate and gather a water sample by flying the present invention into a body of water.

DETAIL DESCRIPTIONS OF THE INVENTION

All illustrations of the drawings are for the purpose of describing selected versions of the present invention and are not intended to limit the scope of the present invention.

Figure 1:
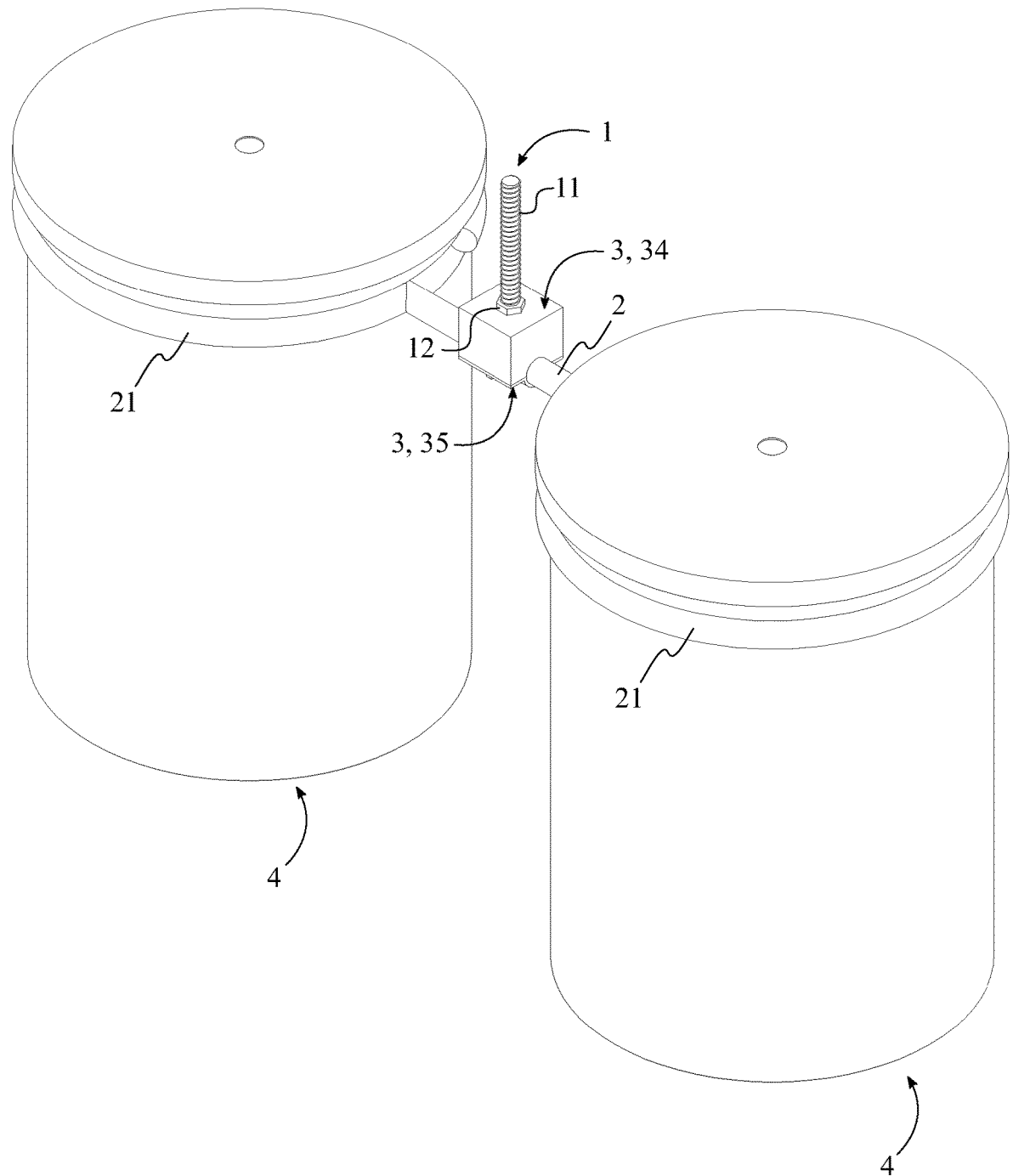
FIG. 1 is a top front perspective view of the present invention.

In reference to FIG. 1, the present invention is an environmental water sampling drone attachment device. The preferred embodiment of the present invention comprises a mounting prong 1, a pivoting clamp 3, a pivot axle 2, at least one mounting harness 21, and at least one container 4. The mounting prong 1 is a rigid shaft that secures the present invention to a (Unmanned Aerial Vehicle) UAV that lands on the water. The pivoting clamp 3 is a rectangular bracket with a channel to receive a cylindrical member. The pivot axle 2 is a cylindrical member that is received by the pivoting clamp 3 and is capable of rotating within the pivoting clamp 3. The mounting harness 21 is a flexible brace that secures the container 4 to the pivot axle 2. The container 4 is a device designed to gather and retain water when placed into a body of water. The mounting prong 1 comprises a male-threaded rod 11 and a nut 12. The pivoting clamp 3 comprising a fixed jaw 34 and a movable jaw 35. The pivoting clamp 3 is terminally connected to the mounting prong 1. As such, the mounting prong 1 is positioned perpendicular to the pivoting clamp 3 thus ensuring the pivoting clamp 3 stays parallel to the body of water. The pivot axle 2 is rotatably coupled to the pivoting clamp 3. Consequently, the pivot axle 2 can rotate within the pivoting clamp 3 with one degree of freedom. More specifically, the pivot axle 2 is rotatably integrated between the fixed jaw 34 and the movable jaw 35 so that the pivot axle 2 can rotate between the fixed jaw 34 and the movable jaw 35 without any horizontal or vertical motion. The mounting harness 21 is connected adjacent to the pivot axle 2. Accordingly, the mounting harness 21 rotates in sync with the rotation of the pivot axle 2. The mounting harness 21 is laterally attached about the container 4. Thus, the container 4 stays secured by the mounting harness 21 when gathering water samples and until the container 4 is removed by the user.

Figure 6:
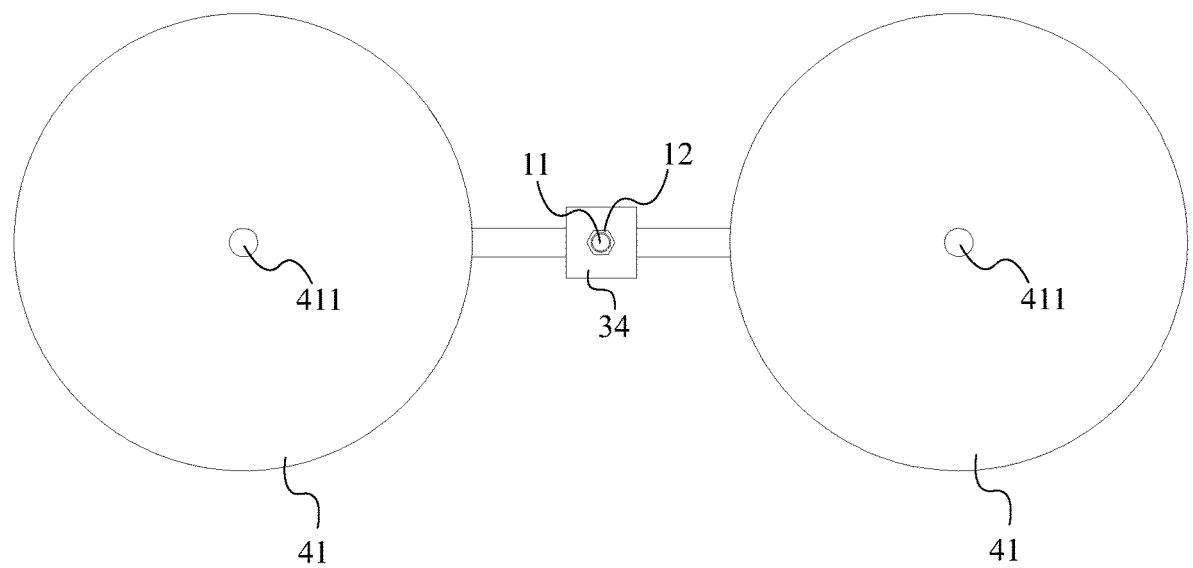
FIG. 6 is a top view of the present invention.
Figure 7:
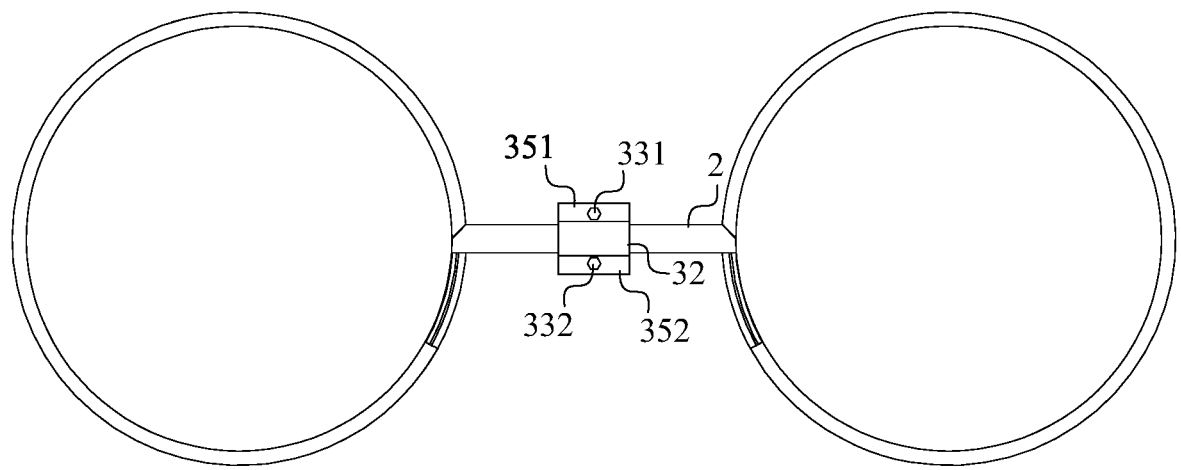
FIG. 7 is a bottom view of the present invention.

Further, the male-threaded rod 11 is terminally connected to the fixed jaw 34. Consequently, the male-threaded rod 11 supports a vertical load from the fixed jaw 34. The nut 12 is threadedly engaged to the male-threaded rod 11. Accordingly, the nut 12 tightens along the male-threaded rod 11 securing the fixed jaw 34 in place. In reference to FIG. 6, the nut 12 is adjacently positioned to the fixed jaw 34. Thus, the nut 12 can rotate independently with respect to the fixed jaw 34.

Furthermore, the fixed jaw 34 comprises a water-facing surface 133, base depression 131, and a plurality of threaded holes 132. The base depression 131 is a curve that receives the pivot axle 2. Each of the plurality of threaded holes 132 is a cylindrical hole that receives a screw thread. The water-facing surface 133 is oppositely positioned to the male-threaded rod 11. As a result, the water-facing surface 133 does not interfere with the male-threaded rod 11. In reference to FIG. 3, the base depression 131 is positioned along the water-facing surface 133. Thus, the base depression 131 receives and enables the rotation of the pivot axle 2. The plurality of threaded holes 132 is distributed across the water-facing surface 133. So, the plurality of threaded holes 132 do not overlap the base depression 131. The plurality of threaded holes 132 is centrally positioned to the base depression 131. So, the plurality of threaded holes 132 is evenly spaced with respect to the base depression 131. The pivot axle 2 is rotatably positioned within the base depression 131. As a result, the pivot axle 2 can rotate while secured in the base depression 131.

Figure 4:
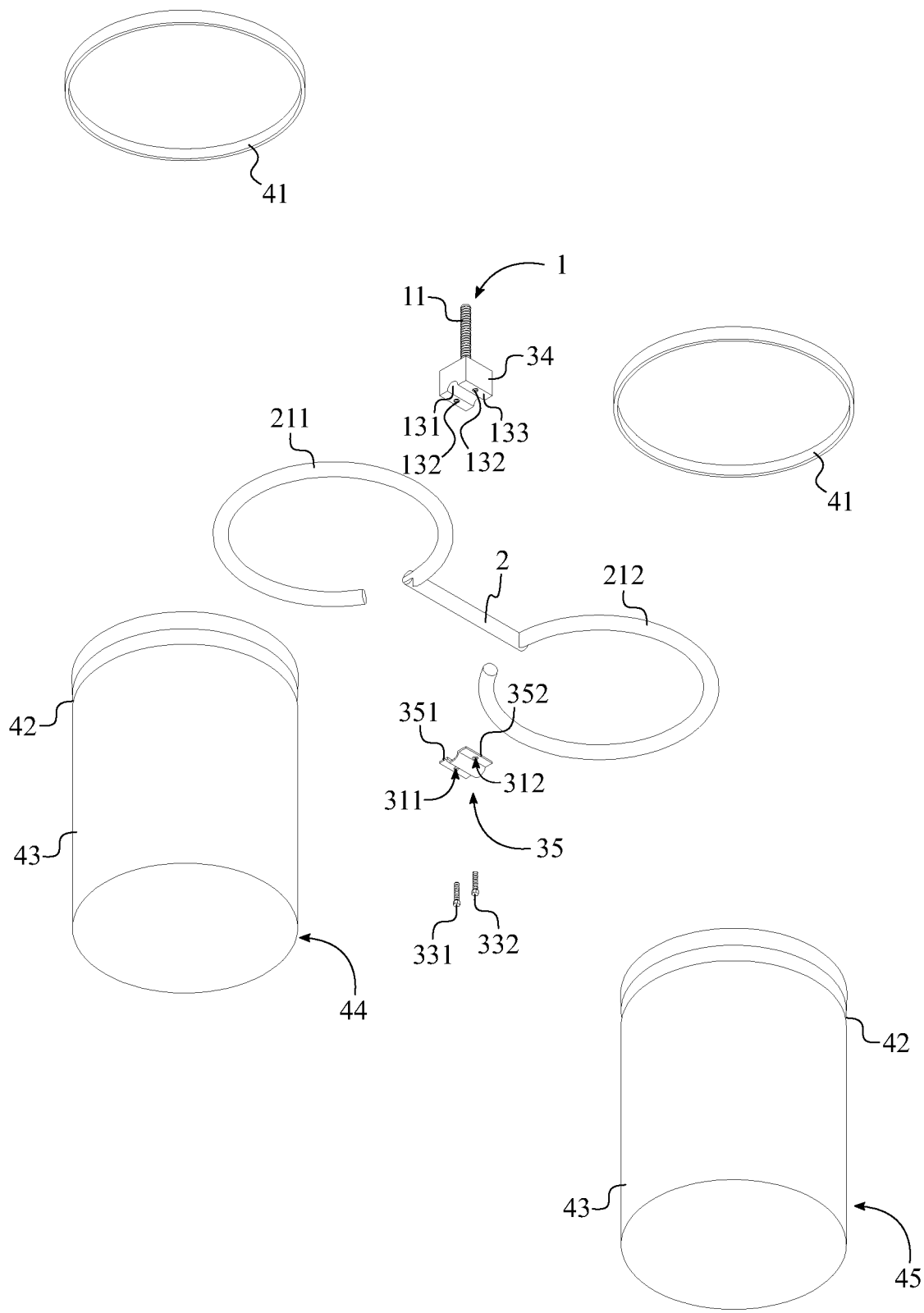
FIG. 4 is a bottom rear exploded perspective view of the present invention.

In reference to FIG. 4, the movable jaw 35 comprises an axle-receiving groove 32, a first clamping plate 351, a second clamping plate 352, and a plurality of holes 31. The axle-receiving groove 32 is a curved structure that can receive the pivot axle 2. The first clamping plate 351 is a rectangular member that is used to attach the movable jaw 35 against the fixed jaw 34. The second clamping plate 352 is another rectangular member that is used to attach the movable jaw 35 against the fixed jaw 34. The first clamping plate 351 is connected adjacent to the axle-receiving groove 32. Thus, the first clamping plate 351 creates a flat member that extends away from the axle-receiving groove 32. The second clamping plate 352 is connected adjacent to the axle-receiving groove 32, opposite to the first clamping plate 351. So, the second clamping plate 352 creates a flush seal with the first clamping plate 351. The plurality of holes 31 is distributed across the axle-receiving groove 32. As a result, the plurality of holes 31 does not overlap the axle-receiving groove 32. The plurality of holes 31 is centrally positioned to the axle-receiving groove 32. Consequently, the plurality of holes 31 is evenly spaced along the movable jaw 35. The plurality of holes 31 traverses through the first clamping plate 351 and the second clamping plate 352. Accordingly, the plurality of holes 31 corresponds to the plurality of threaded holes 132. The pivot axle 2 is rotatably positioned within the axle-receiving groove 32. Thus, the pivot axle 2 can rotate within the axle-receiving groove 32.

Figure 2:
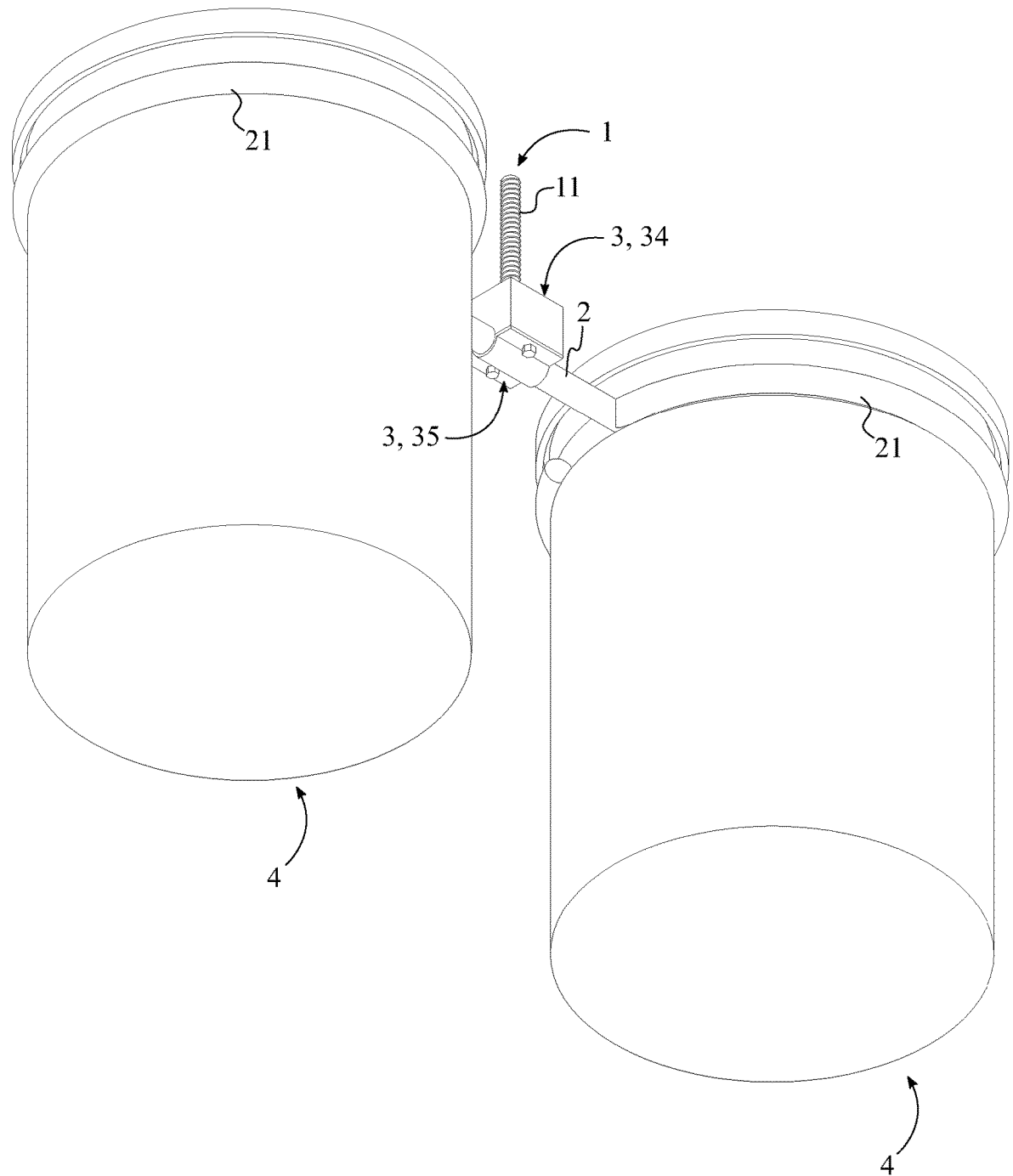
FIG. 2 is a bottom rear perspective view of the present invention.

In reference to FIG. 2, the pivoting clamp 3 further comprises a plurality of bolts 33. The movable jaw 35 is mounted to the fixed jaw 34 by the plurality of bolts 33. So, the movable jaw 35 is secured together to the fixed jaw 34.

Figure 3:
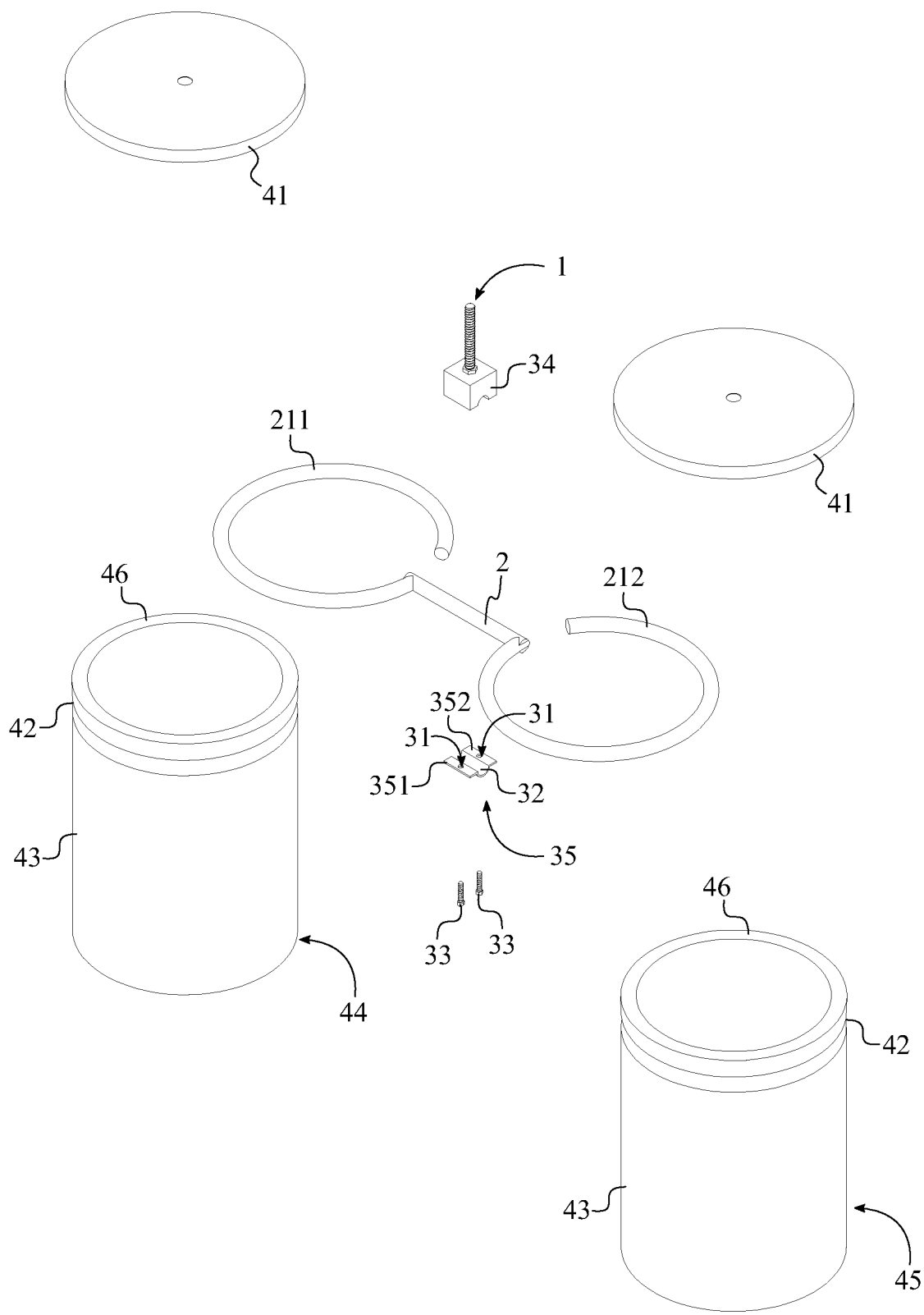
FIG. 3 is a top front exploded perspective view of the present invention.

In reference to FIG. 3, the present invention is designed to secure the pivot axle 2 to allow one degree of freedom for rotational motion. The plurality of holes 31 comprises a first mounting hole 311 and a second mounting hole 312. The plurality of bolts 33 comprises a first fastener 331 and a second fastener 332. The first mounting hole 311 traverses through the first clamping plate 351. The first mounting hole 311 can correspond with the first clamping plate 351. The second mounting hole 312 traverses through the second clamping plate 352. The second mounting hole 312 can correspond with the second clamping plate 352. The first fastener 331 is engaged into a corresponding threaded hole of the plurality of threaded holes 132 through the first mounting hole 311. Consequently, the first fastener 331 secures the movable jaw 35 to the fixed jaw 34 via the first mounting hole 311 and one of the plurality of threaded holes 132. The second fastener 332 is engaged into a corresponding threaded hole of the plurality of threaded holes 132 through the second mounting hole 312. Accordingly, the first second fastener 332 secures the movable jaw 35 to the fixed jaw 34 via the second mounting hole 312 and one of the plurality of threaded holes 132.

Figure 5:
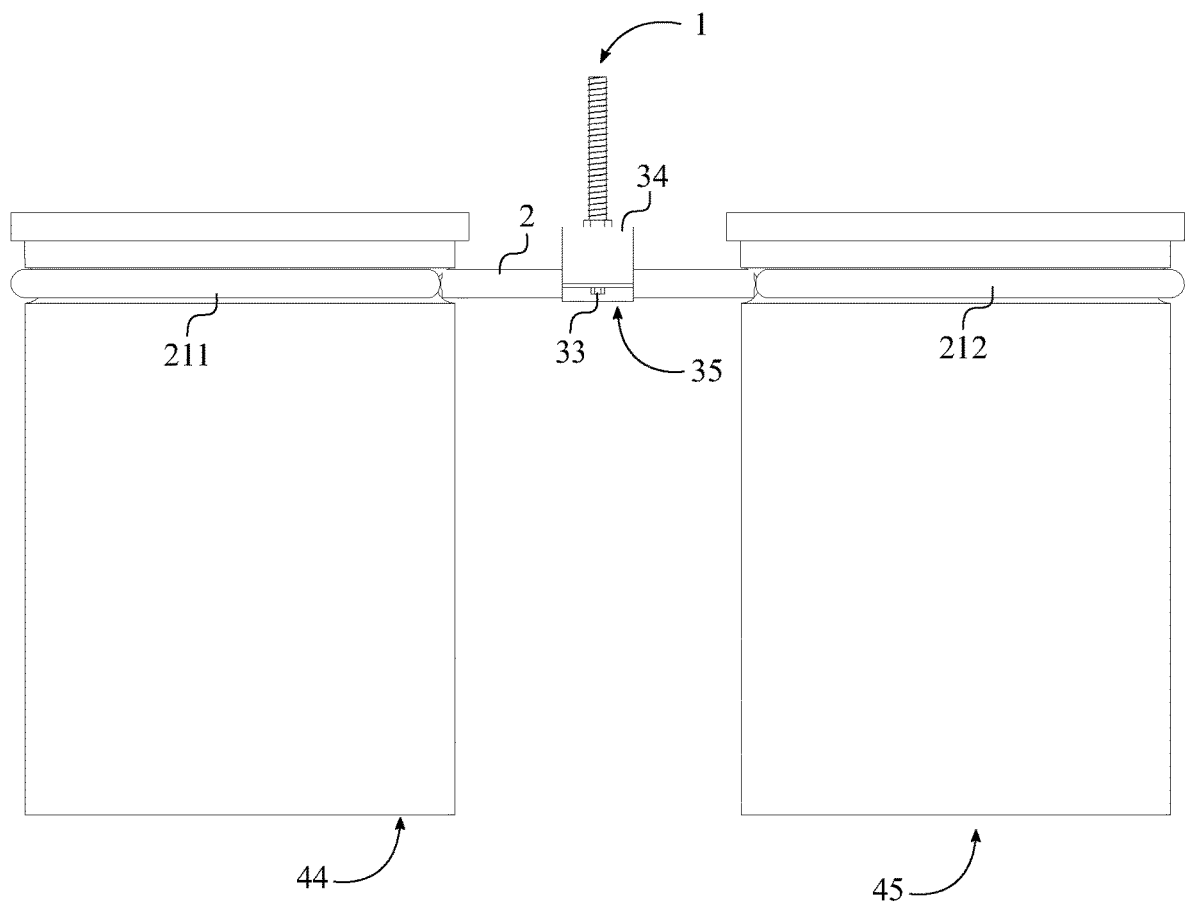
FIG. 5 is a front view of the present invention.

In reference to FIG. 5, the at least one mounting harness 21 is preferably a first mounting harness 211 and a second mounting harness 212. The first mounting harness 211 is a circular shaped ring. The second mounting harness 212 is a circular shaped ring. The first mounting harness 211 is terminally connected to the pivot axle 2. As a result, the first mounting harness 211 rotates with the pivot axle 2. The second mounting harness 212 is terminally connected to the pivot axle 2, opposite to the first mounting harness 211. Consequently, the second mounting harness 212 creates a symmetrically balanced system allowing for easier flight for the UAV. In reference to FIGS. 1, 2, and 4, the pivoting clamp 3 is centrally positioned in between the first mounting harness 211 and the second mounting harness 212. Accordingly, the pivoting clamp 3 allows for rotational motion for the first mounting harness 211 and second mounting harness 212.

Further, the mounting harness 21 is used to hold at least one container 4 that collects the water samples. The at least one container 4 is preferably a first container 44 and a second container 45. Thus, the container 4 can hold water samples when it is positioned under the surface of the water. In reference to FIG. 1, the first mounting harness 211 is laterally attached about the first container 44. So, the first container 44 is secured to the UAV by the first mounting harness 211. The second mounting harness 212 is laterally attached about the second container 45. As a result, the second container 45 is secured to the UAV by the second mounting harness 212.

In reference to FIG. 4, the container 4 comprises a receptacle 43, a mounting groove 42, and a lid 41. The receptacle 43 is an enclosure with a circular opening. The lid 41 is a circular cover that closes around the receptacle 43. The mounting groove 42 laterally traverses around the receptacle 43. Consequently, the mounting groove 42 allows the container 4 to be secured by the mounting harness 21. The mounting groove 42 is positioned across the edge of the receptacle 43. As a result, the mounting groove 42 does not interfere with the opening and closing of the container 4. The lid 41 is mounted across the rim 46 of the receptacle 43. Thus, the lid 41 covers the container 4 and seals a water sample within the container 4.

Furthermore, the container 4 of the present invention is used to retain water samples throughout the flight of the UAV. In reference to FIG. 1, the container 4 further comprises a one-way valve 411. The one-way valve 411 allows water to only flow into the container 4. The one-way valve 411 is integrated into the lid 41. So, the water samples are sealed within the container 4 until the lid 41 is removed by the user.

Although the invention has been explained in relation to its preferred embodiment, it is to be understood that many other possible modifications and variations can be made without departing from the spirit and scope of the invention as hereinafter claimed.

What is claimed is:

1. An environmental water sampling drone attachment device comprising:
   a mounting prong;
   a pivoting clamp;
   a pivot axle;
   at least one mounting harness;
   at least one container;
   the mounting prong comprising a male-threaded rod and a nut;
   the pivoting clamp comprising a fixed jaw and a movable jaw;
   the pivoting clamp being connected to the mounting prong;
   the pivot axle being rotatably coupled to the pivoting clamp;
   the mounting harness being connected adjacent to the pivot axle;
   the mounting harness being laterally attached about the container; and
   the pivot axle being rotatably integrated between the fixed jaw and the movable jaw.

2. The environmental water sampling drone attachment device as claimed in claim 1:
   the male-threaded rod being terminally connected to the fixed jaw;
   the nut being threadedly engaged to the male-threaded rod; and
   the nut being adjacently positioned to the fixed jaw.

3. The environmental water sampling drone attachment device as claimed in claim 1 comprising:
   the fixed jaw comprising a water-facing surface, a base depression, and a plurality of threaded holes;
   the water-facing surface being oppositely positioned to the male-threaded rod;
   the base depression being positioned along the water-facing surface;
   the plurality of threaded holes being distributed across the water-facing surface;
   the plurality of threaded holes being centrally positioned to the base depression; and the pivot axle being rotatably positioned within the base depression.

4. The environmental water sampling drone attachment device as claimed in claim 1 comprising:
the movable jaw comprising an axle-receiving groove, a first clamping plate, a second clamping plate, and a plurality of holes;
the first clamping plate being connected adjacent to the axle-receiving groove;
the second clamping plate being connected adjacent to the axle-receiving groove, opposite to the first clamping plate;
the plurality of holes being distributed across the axle-receiving groove;
the plurality of holes being centrally positioned to the axle-receiving groove;
the plurality of holes traversing through the first clamping plate and the second clamping plate; and
the pivot axle being rotatably positioned within the axle-receiving groove.

5. The environmental water sampling drone attachment device as claimed in claim 1 comprising:
the pivoting clamp further comprising a plurality of bolts; and
the movable jaw being mounted to the fixed jaw by the plurality of bolts.

6. The environmental water sampling drone attachment device as claimed in claim 5 comprising:
the fixed jaw comprising a plurality of threaded holes;
the movable jaw comprising a first clamping plate, a second clamping plate, and a plurality of holes;
the plurality of holes comprising a first mounting hole and a second mounting hole;
the plurality of bolts comprising a first fastener and a second fastener;
the first mounting hole traversing through the first clamping plate;
the second mounting hole traversing through the second clamping plate;
the first fastener being engaged into a corresponding threaded hole of the plurality of threaded holes through the first mounting hole; and
the second fastener being engaged into a corresponding threaded hole of the plurality of threaded holes through the second mounting hole.

7. The environmental water sampling drone attachment device as claimed in claim 1 comprising:
the at least one mounting harness being a first mounting harness and a second mounting harness;
the first mounting harness being terminally connected to the pivot axle;
the second mounting harness being terminally connected to the pivot axle, opposite to the first mounting harness; and
the pivoting clamp being centrally positioned in between the first mounting harness and the second mounting harness.

8. The environmental water sampling drone attachment device as claimed in claim 7 comprising:
the at least one container being a first container and a second container;
the first mounting harness being laterally attached about the first container; and
the second mounting harness being laterally attached about the second container.

9. The environmental water sampling drone attachment device as claimed in claim 1 comprising:
the container comprising a receptacle, a mounting groove, and a lid;
the mounting groove laterally traversing around the receptacle;
the mounting groove being positioned offset from a rim on the receptacle; and
the lid being mounted across the rim of the receptacle.

10. The environmental water sampling drone attachment device as claimed in claim 9 comprising:
the container further comprising a one-way valve; and
the one-way valve being integrated into the lid.

11. An environmental water sampling drone attachment device comprising:
a mounting prong;
a pivoting clamp;
a pivot axle;
at least one mounting harness;
at least one container;
the mounting prong comprising a male-threaded rod and a nut;
the pivoting clamp comprising a fixed jaw and a movable jaw;
the fixed jaw comprising a water-facing surface, a base depression, and a plurality of threaded holes;
the movable jaw comprising an axle-receiving groove, a first clamping plate, a second clamping plate, and a plurality of holes;
the pivoting clamp being connected to the mounting prong;
the pivot axle being rotatably coupled to the pivoting clamp;
the mounting harness being connected adjacent to the pivot axle;
the mounting harness being laterally attached about the container;
the pivot axle being rotatably integrated between the fixed jaw and the movable jaw;
the pivot axle being rotatably positioned within the base depression and the axle-receiving groove; and
the container comprising a receptacle, a mounting groove, and a lid.

12. The environmental water sampling drone attachment device as claimed in claim 11,
the male-threaded rod being terminally connected to the fixed jaw;
the nut being threadedly engaged to the male-threaded rod; and
the nut being adjacently positioned to the fixed jaw.

13. The environmental water sampling drone attachment device as claimed in claim 11 comprising:
the water-facing surface being oppositely positioned to the male-threaded rod;
the base depression being positioned along the water-facing surface;
the plurality of threaded holes being distributed across the water-facing surface; and
the plurality of threaded holes being centrally positioned to the base depression.

14. The environmental water sampling drone attachment device as claimed in claim 11 comprising:
the first clamping plate being connected adjacent to the axle-receiving groove;
the second clamping plate being connected adjacent to the axle-receiving groove, opposite to the first clamping plate;
the plurality of holes being distributed across the axle-receiving groove;

the plurality of holes being centrally positioned to the axle-receiving groove; and the plurality of holes traversing through the first clamping plate and the second clamping plate.

15. The environmental water sampling drone attachment device as claimed in claim 11 comprising:

the pivoting clamp further comprising a plurality of bolts; and the movable jaw being mounted to the fixed jaw by the plurality of bolts.

16. The environmental water sampling drone attachment device as claimed in claim 15 comprising:

the plurality of holes comprising a first mounting hole and a second mounting hole;

the plurality of bolts comprising a first fastener and a second fastener;

the first mounting hole traversing through the first clamping plate;

the second mounting hole traversing through the second clamping plate;

the first fastener being engaged into a corresponding threaded hole of the plurality of threaded holes through the first mounting hole; and the second fastener being engaged into a corresponding threaded hole of the plurality of threaded holes through the second mounting hole.

17. The environmental water sampling drone attachment device as claimed in claim 11 comprising:

the at least one mounting harness being a first mounting harness and a second mounting harness;

the first mounting harness being terminally connected to the pivot axle;

the second mounting harness being terminally connected to the pivot axle, opposite to the first mounting harness; and the pivoting clamp being centrally positioned in between the first mounting harness and the second mounting harness.

18. The environmental water sampling drone attachment device as claimed in claim 17 comprising:

the at least one container being a first container and a second container;

the first mounting harness being laterally attached about the first container; and the second mounting harness being laterally attached about the second container.

19. The environmental water sampling drone attachment device as claimed in claim 11 comprising:

the mounting groove laterally traversing around the receptacle;

the mounting groove being positioned offset from a rim on the receptacle; and the lid being mounted across the rim of the receptacle.

20. The environmental water sampling drone attachment device as claimed in claim 19 comprising:

the container further comprising a one-way valve; and the one-way valve being integrated into the lid.

* * * * *